(12) United States Patent
Tharaux et al.

(10) Patent No.: US 8,586,822 B2
(45) Date of Patent: Nov. 19, 2013

(54) METHODS FOR PRODUCING A NON HUMAN MODEL FOR AORTIC ANEURYSM

(75) Inventors: Pierre Louis Tharaux, Paris (FR); Hafid Ait-Oufella, Paris (FR); Alain Tedgui, Paris (FR); Ziad Mallat, Paris (FR)

(73) Assignee: INSERM (Institut National de la Sante et de la Recherche Medicale), Paris (FR)

( * ) Notice: Subject to any disclaimer, the term of this patent is extended or adjusted under 35 U.S.C. 154(b) by 612 days.

(21) Appl. No.: 12/740,405

(22) PCT Filed: Sep. 30, 2008

(86) PCT No.: PCT/EP2008/063100
§ 371 (c)(1),
(2), (4) Date: Apr. 29, 2010

(87) PCT Pub. No.: WO2009/056419
PCT Pub. Date: May 7, 2009

(65) Prior Publication Data
US 2010/0260726 A1    Oct. 14, 2010

(30) Foreign Application Priority Data
Nov. 2, 2007 (EP) .................................. 07301521

(51) Int. Cl.
*A01K 67/00* (2006.01)
*C12N 15/00* (2006.01)

(52) U.S. Cl.
USPC .................................................. 800/21; 800/8

(58) Field of Classification Search
None
See application file for complete search history.

(56) References Cited

U.S. PATENT DOCUMENTS

2003/0078190 A1    4/2003  Weinberg

FOREIGN PATENT DOCUMENTS

WO          01/30370          5/2001
WO   WO 2007050793 A2 *   5/2007

OTHER PUBLICATIONS

Habashi et al. Losartan, an AT1 Antgonist, Prevents Aortic Aneurism in a Mouse Model of Marfan Syndrome. Science, 2006. 312:117-120.*
Carrell et al, Experimental techniques and models in the study of development and treatment of aortic aneurysm. British Journal of Surgery, 1999. 86:305-312.*
Buono et al, B7-1/B7-2 Costimulation Regulates Plaque Antigen-Specific T-Cell Responses and Atherogenesis in Low-Density Lipoprotein Receptor-Deficient Mice, Circulation, 2004.109:2009-2015.*
Daugherty and Cassis, Mouse Models of Abdominal Aortic Aneurysms. Arterioscler Thromb Vasc Biology, 2004. 429-434.*
Arbustini et al., "Aneurysm syndromes and TGF-beta receptor mutations," N. Eng. J. Med., 355(20):2155 (2006).
Loeys et al., "Aneurysm syndromes caused by mutations in the TGF-beta receptor," N. Eng. J. Med., 355(8):788-798 (2006).
Office Action in EP 08804927.5, dated Nov. 22, 2011.
Pannu et al., "Genetic basis of thoracic aortic aneurysms and aortic dissections," Am. J. Med. Genet., 139C(1):10-16 (2005).
International Search Report in PCT/EP08/63100, dated Mar. 4, 2009.
Dai et al., Circulation, 112(7):1008-1015 (2005).
Pannu et al., Circulation, 12(4):513-520 (2005).
Daugherty et al., Arteriosclerosis Thromb. Vascular Biol., 24(3):429-434 (2004).
Manning et al., Arteriosclerosis Thromb. Vascular Biol., 23(1):483-488 (2003).

* cited by examiner

*Primary Examiner* — Joseph T. Woitach
*Assistant Examiner* — Kimberly A Aron
(74) *Attorney, Agent, or Firm* — McAndrews, Held & Malloy Ltd.

(57) ABSTRACT

The present invention relates to methods for producing a non human animal model for aortic aneurysm which could provide insight into the diagnosis and treatment of disease. Furthermore, the present invention relates to methods and compositions for the treatment or the prevention of aneurysm in a subject in need thereof.

10 Claims, 8 Drawing Sheets

METHODS FOR PRODUCING A NON HUMAN MODEL FOR AORTIC ANEURYSM

The present application is filed pursuant to 35 U.S.C. 371 as a U.S. National Phase application of International Patent Application No. PCT/EP08/63100, which was filed Sep. 30, 2008, claiming the benefit of priority to European Patent Application No. 07301521.6, which was filed on Nov. 2, 2007. The entire text of the aforementioned applications is incorporated herein by reference in its entirety.

FIELD OF THE INVENTION

The present invention relates to methods for producing a non human animal model for aortic aneurysm which could provide insight into the diagnosis and treatment of said disease. Furthermore, the present invention relates to methods and compositions for the treatment or the prevention of aneurysm in a subject in need thereof.

BACKGROUND OF THE INVENTION

Aortic aneurysm is a chronic degenerative disease characterized by segmental weakening and dilatation of the vascular wall.

Aortic aneurysms are commonly classified according to their anatomical location. Thoracic aortic aneurysms (TAAs) involve the ascending aorta, arch or descending aorta; Aneurysms of the ascending thoracic aorta most often result from cystic medial degeneration, which appears histologically as smooth muscle cell dropout and elastic fiber degeneration. Medial degeneration leads to weakening of the aortic wall, which in turn results in aortic dilatation and aneurysm formation. Cystic medial degeneration occurs normally to some extent with aging, but the process is accelerated by hypertension (reviewed in Isselbacher E M, Circulation. 2005; 111: 816-828.). There are a number of conditions that predispose a person to develop defects of the inner lining of the aorta, including hypertension, Marfan's disease, Ehlers-Danlos syndrome, connective tissue diseases, Turner syndrome, bicuspid aortic valve, Familial Thoracic Aortic Aneurysm Syndrome, and defects of heart development which begin during fetal development. A dissection can also occur accidentally following insertion of a catheter, trauma, or surgery. Abdominal aortic aneurysms (AAAs) affect the part of the aorta in the abdominal cavity. AAA are much more common than thoracic aortic aneurysms. Age is an important risk factor, and the incidence of abdominal aortic aneurysm rises rapidly after the age of 55 years in men and 70 in women. Recent estimates indicate that the prevalence of AAA is 4% to 9% in adults older than 65 years old. AAA is strongly associated with local aortic wall and systemic atherosclerosis, but a clear causal relationship is not established (reviewed in Isselbacher Circulation 2005 and Faxon D P, Circulation. 2004 Jun. 1; 109(21):2617-25). Etiologic factors include genetic susceptibility; 15% to 20% of patients have a family history. AAA is much more common (2 to 5 times) in men than in women and more common in white than black populations. Cigarette smoking is a major risk factor for AAA. The natural history is a gradual enlargement of the aneurysm until it exceeds 5.5 cm, when risk of rupture rises exponentially (Thompson R W, Geraghty P J, Lee J K. Abdominal aortic aneurysms: basic mechanisms and clinical implications. Curr Probl Surg. 2002; 39: 110-230). The primary pathophysiological process is chronic transmural inflammation with destruction of the media, including loss of elastic fibers and SMCs. Elevation of inflammatory markers such as interleukin-6 and elevation of proteinases such as MMP9 and elastin are correlated with AAA and the expansion rate. Doxycycline inhibits MMP activity and can reduce AAA in experimental animals. Clinical trials have shown a reduction in MMP9 levels with doxycycline but not a reduction in expansion rate in preliminary studies. Other agents such as roxithromycin have shown modest effects as well.

Currently, the only available treatments for aortic aneurysm are surgical resection and replacement or more recently, insertion of an endovascular stent. Then, patients are usually given long term treatment with drugs to reduce their hypertension.

Therefore, there is a need to provide new drugs that will help the physician to prevent or treat aortic aneurysm Furthermore, a major problem in the management of aortic aneurysms is that the symptoms of an aortic aneurysm often do not surface until the aneurysm is quite large. Therefore, a timely diagnosis may be suitable to envisage an early intervention and dramatic improvement in the chances for survival.

However, in both cases, there is a permanent need in the art for seeking animal models for aortic aneurysms to provide insight into potential mechanisms in the development and treatment of disease.

Several mouse models of aortic aneurysms have been developed that use a diverse array of methods for producing the disease, including genetic manipulation and chemical induction (Daugherty et al. Arterioscler. Thromb Vase Biol. 2004 March; 24(3):429-34). The models recapitulate some facets of the human disease including medial degeneration, inflammation, thrombus formation, and rupture. Genetic models include defects in extracellular matrix maturation, increased degradation of elastin and collagen, aberrant cholesterol homeostasis, and enhanced production of angiotensin peptides. The chemical approaches include the intraluminal infusion of elastase, periaortic incubations of calcium chloride, and subcutaneous infusion of AngII. For example Daugherty A. et al. (2000) developed a mouse model wherein angiotensin II is continuously infused into mature apoE deficient mice.

However, there is still a need in the art to provide reliable animal models for aortic aneurysm that are reproducible (for example AAA incidence in the AII/ApoE deficient mouse model ranged from 14%, see Babamusta F et al Atherosclerosis. 2006 June; 186(2):282-90, to more than 60%) and do not involve any surgical treatment (unlike elastase or calcium chloride model) to provoke an aneurysm to develop or occur.

SUMMARY OF THE INVENTION

The present invention relates to a method for producing a non human animal model for aortic aneurysm comprising the steps consisting of:
  a) providing a non human animal
  b) increasing the arterial blood pressure of said animal
  c) inhibiting the activity of Transforming Growth Factor Beta (TGF-beta) in said animal The present invention also relates to a method for producing a non human animal model for aortic aneurysm comprising the steps consisting of:
  a) providing a non human animal
  b) increasing the arterial blood pressure of said animal
  c) reducing the number or the activity of Treg cells in said animal The present invention also relates to TGF-beta or variant thereof for the treatment or the prevention of aneurysm.

The present invention also relates to a cellular composition comprising Treg cells for the treatment or the prevention of aneurysm.

DETAILED DESCRIPTION OF THE INVENTION

Definitions

The term "expression" when used in the context of expression of a gene or nucleic acid refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include messenger RNAs which are modified, by processes such as capping, polyadenylation, methylation, and editing, and proteins (e.g., TGF-beta) modified by, for example, methylation, acetylation, phosphorylation, ubiquitination, SUMOylation, ADP-ribosylation, myristilation, and glycosylation.

An "inhibitor of expression" refers to a natural or synthetic compound that has a biological effect to inhibit or significantly reduce the expression of a gene.

As used herein, "TGF-beta," unless otherwise specifically indicated, refers to any one or more isoforms of TGF-beta. Likewise, the term "TGF-beta receptor," unless otherwise indicated, refers to any receptor that binds to or transduces signal in response to at least one TGF-beta isoform. Currently, there are 5 known isoforms of TGF-beta (1, 2, 3, 4 and 5), all of which are homologous among each other (60-80% identity), form homodimers of about 25 kDa, and act upon common TGF-beta receptors (T[beta]R-I, T[beta]R-II, T[beta]R-IIB, and T[beta]R-III). TGF-beta1, TGF-beta2, and TGF-beta3 are found in mammals. The structural and functional aspects of TGF-beta as well as TGF-beta receptors are well known in the art (see, for example, Cytokine Reference, eds. Oppenheim et al., Academic Press, San Diego, Calif., 2001). TGF-beta is remarkably conserved among species.

The term "Variant" refers to polypeptide of in which a given amino acid residue has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared. Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

The term "TGF-beta activity" encompasses all the biological effects of TGF-beta, including the activation of SMAD2/SMAD3 and SMAD4 or other SMAD-independent effects (such as MAPK activation).

The terms "inhibitor," "inhibit," "neutralize," "antagonize," and their cognates refer to the ability of a compound to act as an antagonist of a certain reaction or biological activity. The decrease in the amount or the biological activity is preferably at least about 10%, 20%, 30%, 40%, 50%, 60%, 70%, 80%, 90%, or more. The terms may also refer to a decrease in the relative amount of at least one protein that is responsible for the biological activity of interest (e.g., TGF-beta, TGF-beta receptor).

As used herein, "TGF-beta antagonist" generally refers to any compound that directly downregulates the biological activity of TGF-beta. A molecule "directly downregulates" the biological activity of TGF-beta if it downregulates the activity by interacting with a TGF-beta gene, a TGF-beta transcript, a TGF-beta ligand, or a TGF-beta receptor. A TGF-beta antagonist may, for example, bind to- and neutralize the activity of TGF-beta; affect stability or conversion of the precursor molecule to the active, mature form; interfere with the binding of TGF-beta to one or more receptors; or it may interfere with intracellular signaling of a TGF-beta receptor. Methods for assessing neutralizing biological activity of TGF-beta antagonists are known in the art.

The term "anti-TGF-beta antibody" refers to an antibody or a fragment thereof which recognizes TGF-beta.

As used herein, the term "T cells" includes lymphocytes which express phenotypic markers and rearrangements of the TCRbeta locus with or without rearrangements of the TCRalpha. Phenotypic markers include expression of CD4 and/or CD8.

As used herein, the term "regulatory T cells" or "Treg" cells refers to naturally occurring T cells which express the cell surface markers CD4+ and CD25+, which express FoxP3 protein as measured by a Western blot and/or FoxP3 mRNA transcript and to T cells of the Tr1 or TH3-like phenotype whose regulatory function depend on IL-10 and/or TGF-beta and may or may not express foxp3.

The term "Treg cell depleting agent," as used herein, refers to any agent that reduces Treg cell circulating levels in an organism or that reduces or interferes with the activity of Treg cells in an organism.

Methods for Producing a Non Human Model for Aneurysm

An object of the invention relates to a method for producing a non human animal model for aortic aneurysm comprising the steps consisting of:
a) providing a non human animal
b) increasing the arterial blood pressure of said animal
c) inhibiting the activity of Transforming Growth Factor Beta (TGF-beta) in said animal In a particular embodiment, inhibition of TGF-beta is performed with a TGF-beta antagonist.

More particularly, the TGF-beta antagonist may be a low molecular weight inhibitor, e.g. a small organic molecule.

Alternatively, the TGF-beta antagonist may be an anti-TGF-beta antibody or anti-TGF-beta-receptor antibody.

In some embodiments, the TGF-beta antagonist is an antibody that blocks TGF-beta binding to its receptor. The antibody is such that it specifically binds to at least one isoform of TGF-beta or to the extracellular domain of at least one TGF-beta receptor.

Antibodies directed against the TGF-beta or TGF-beta receptor can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred.

Monoclonal antibodies against TGF-beta or TGF-beta receptor can be prepared and isolated using any technique that provides for the production of antibody molecules by continuous cell lines in culture. Techniques for production and isolation include but are not limited to the hybridoma technique originally described by Kohler and Milstein (1975); the human Treg cell-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-TGF-beta or TGF-beta receptor, single chain antibodies. TGF-beta or TGF-beta receptor antibodies useful in practicing the present invention also include anti-TGF-beta or TGF-beta receptor fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to TGF-beta or TGF-beta receptor.

Examples of monoclonal or polyclonal antibodies directed against one or more isoforms of TGF-beta include those described in U.S. Pat. No. 5,571,714; or in International patent application WO 97/13844, or WO 00/66631.

In nonlimiting illustrative embodiments, the anti-TGF-beta antibody may the a murine monoclonal antibody 1D11 produced by the hybridoma 1D11.16 (ATCC Deposit Designation No. 9849, also described in U.S. Pat. Nos. 5,571,714; 5,772,998; and 5,783,185). The sequence of the 1D11 heavy chain variable region is available under accession No. AAB46787.

Another example of anti-TGF-beta antibody may be the murine monoclonal antibody 2G7 as described by Lucas C. et al. (1990).

Example of monoclonal or polyclonal antibodies directed against one or more isoforms of TGF-beta receptor include those described in Gorelik L et al. (2002) Nat. Rev. Immunol., 2(1):46-53; U.S. Pat. No. 5,693,607; U.S. Pat. No. 6,001,969; U.S. Pat. No. 6,008,011; U.S. Pat. No. 6,010,872; WO 92/00330; WO 93/09228; WO 95/10610; and WO 98/48024.

Alternatively, the TGF-beta antagonist may be an aptamer having affinity with TGF-beta or TGF-beta receptor.

Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996).

Other examples of TGF-beta antagonists include but are not limited to: dominant negative and soluble TGF-beta receptors, LAP (WO 91/08291), LAP-associated TGF-beta (WO 94/09812); TGF-beta-binding glycoproteins/proteoglycans such as fetuin (U.S. Pat. No. 5,821,227); decorin, biglycan, fibromodulin, lumican, and endoglin (U.S. Pat. No. 5,583,103; U.S. Pat. No. 5,654,270; U.S. Pat. No. 5,705,609; U.S. Pat. No. 5,726,149; U.S. Pat. No. 5,824,655; U.S. Pat. No. 5,830,847; U.S. Pat. No. 6,015,693; WO 91/04748; WO 91/10727; WO 93/09800; and WO 94/110187); mannose-6-phosphate or mannose-1-phosphate (U.S. Pat. No. 5,520,926); prolactin (WO 97/40848); insulin-like growth factor II (WO98/17304); extracts of plants, fungi and bacteria (EP 813875; JP 8119984; and U.S. Pat. No. 5,693,610); proteins involved in TGF-beta signaling, including SMADs and MADs (EP 874046; WO 97/31020; WO 97/38729; WO 98/03663, WO 98/07735; WO 98/07849; WO 98/45467; WO 98/53068; WO 98/55512; WO 98/56913; WO 98/53830; WO 99/50296; WO 99/01765; U.S. Pat. No. 5,834,248; U.S. Pat. No. 5,807,708; and U.S. Pat. No. 5,948,639, U.S. Pat. No. 6,824,971 B1; U.S. Pat. No. US2005/164295 (A1) and), Ski and Sno (Stroschein et al. (1999) Science, 286:771-774); and any mutants, fragments, or derivatives of the above-identified molecules that retain the ability to directly inhibit the biological activity of TGF-beta.

In a particular embodiment, inhibition of TGF-beta may be performed with an inhibitor of TGF-beta gene expression or an inhibitor of TGF-beta-receptor gene expression.

Inhibitors of TGF-beta or TGF-beta receptor gene expression for use in the present invention may be also based on anti-sense oligonucleotide constructs. Anti-sense oligonucleotides, including anti-sense RNA molecules and anti-sense DNA molecules, would act to directly block the translation of TGF-beta or TGF-beta receptor mRNA by binding thereto and thus preventing protein translation or increasing mRNA degradation, thus decreasing the level of TGF beta or TGF-beta-receptors, and thus activity, in a cell. For example, antisense oligonucleotides of at least about 15 bases and complementary to unique regions of the mRNA transcript sequence encoding TGF-beta or TGF-beta receptor can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of TGF-beta or TGF-beta receptor expression for use in the present invention. TGF-beta or TGF-beta receptor expression can be reduced by contacting a subject or cell with a small double stranded RNA (dsRNA), or a vector or construct causing the production of a small double stranded RNA, such that TGF-beta or TGF-beta receptor expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

shRNAs (short hairpin RNA) can also function as inhibitors of TGF-beta or TGF-beta receptor expression for use in the present invention Ribozymes can also function as inhibitors of TGF-beta or TGF-beta receptor gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of TGF-beta or TGF-beta receptor mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable.

Both antisense oligonucleotides and ribozymes useful as inhibitors of TGF-beta or TGF-beta receptor gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and preferably cells expressing TGF-beta or TGF-beta receptor. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated (AAV) viruses, which are double-stranded DNA viruses that have already been approved for use in gene therapy. Actually 12 different AAV serotypes (AAV1 to 12) are known, each with different tissue tropisms (Wu, Z Mol Ther 2006; 14:316-27). Recombinant AAV are derived from the dependent parvovirus AAV2 (Choi, V W J Virol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages; and lack of superinfection inhibition thus allowing multiple series of transductions. Reportedly, the adeno-associated virus can integrate into cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUCI9, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter.

Alternatively, the animal may be deficient for a gene or a plurality of genes so that said animal cannot produce or activate TGF-beta. For example, said animal may be deficient in a gene selected from the group consisting of TGF-beta itself, TGF-beta receptors, TGF-beta signalling molecules (SMADS) or genes known to be involved in the modulation of TGF-beta activity, such as integrins alpha(v)-beta6 or alpha (v)-beta8 or BMP-7

Deficient animals, especially deficient mice are generally commercially available. However, methods for producing deficient animal or knock-out animal are well known in the art. For example, Knock-out animals comprising targeted mutations are achieved routinely in the art as provided for example by the method by Joyner, A. L. (Gene Targeting. 1999, Second Edition, The Practical Approach Series, Oxford University Press, New York) and Hogan, B., et al. (Manipulating the mouse embryo. 1994, Second Edition, Cold Spring Harbor Press, Cold Spring Harbor.). For example, the heterozygous and/or homozygous knock-out animal of the above-described methods may be generated by selecting embryonic stem (ES) cell clones carrying a mutated allele for the gene of interest, verifying the targeted mutation in the recombinant embryonic stem cell clones, injecting the verified recombinant embryonic stem cells into blastocysts of wild type animals, transferring these injected blastocysts into pseudo-pregnant foster mothers, breeding chimeras resulting from the blastocysts to wild type animals, testing the offspring resulting from these breedings for the presence of the targeted mutation, breeding heterozygous animals, optionally to generate homozygous knock-out animals. Embryonic stem cells used in the art which may also be used in the methods of this invention comprise for example embryonic stem cells derived from mouse strains such as C57BL/6, BALB/c, DBA/ 2, CBA/ and SV129. Preferably, embryonic stem cells derived from C57BL/6 mice are used (Seong, E et al (2004) Trends Genet. 20, 59-62; Wolfer, D. P. et al., Trends Neurosci. 25 (2002): 336-340). Methods for producing deficient animals are also described in WO03037074 and US2007056052.

Alternatively, the knock out of the targeted gene may be performed in conditional manner as described in WO2006048466 or WO2006048465, so that the disruption of expression may be performed at a willing time and/or in a specific tissue or cells.

It is well established that one of the effects of TGF-beta inhibition is an impaired function of regulatory T cells or Treg cells (for review, see Horwitz, Immunity, 2006. Indeed, it has been shown that TGF-beta can promote the generation and expansion of CD4+CD25+ regulatory T cells (Yamagiwa et al., J Immunol, 2001; Peng et al., PNAS, 2004) and can induce a regulatory phenotype in CD4+CD25− T cells (Chen et al., J Exper Med 2003; Fantini et al., J Immunol, 2004).

A further object of the invention therefore relates to a method for producing a non human animal model for aortic aneurysm comprising the steps consisting of:
a) providing a non human animal
b) increasing the arterial blood pressure of said animal
c) reducing the number or the activity of Treg cells in said animal.

In a particular embodiment, the invention relates to a method for producing a non human animal model for aortic aneurysm comprising the steps consisting of:

a) providing a non human animal
b) increasing the arterial blood pressure of said animal
c) reducing the number or the activity of Treg cells in said animal
wherein reducing the number or the activity of Treg cells is performed by inhibiting the activity of Transforming Growth Factor beta (TGB-beta) in said animal.

Typically, inhibiting the activity of TGF-beta can be performed according to any one the method steps described above.

In a particular embodiment, a Treg cell depleting agent is used at step c). Depletion of endogenous Treg cells can be effected by any method known in the art. Treg cell depleting agents include hormones, growth factors, antibodies, antibody fragments, antibody mimics, and their genetically or enzymatically engineered counterparts.

Preferably, the Treg cell depleting agent has the ability to recognize and bind to an antigen or receptor associated with Treg cells. Preferred Treg cell depleting agents for use in the present invention are antibodies and antibody mimics capable of recognizing and inactivating Treg cells. Preferably, such antibodies are directed against cell surface antigens expressed on Treg cells. Examples of specific antibodies directed against cell surface antigens on Treg cells include without limitation, antibodies against CD25, CCR7, B7, Foxp3, CCR4, and CCR8). Such antibodies may be produced according to the methods as above described.

Alternatively Treg cell depleting agent include cytotoxic drugs that specifically kill Treg cells.

In another embodiment, an inhibitor of gene expression may be used at step c), said gene may be selected form the group consisting of CD28, CCR7, Foxp3, CD25, B7, CCR4, CCR8, ICOS and CCL1. Said inhibitors of expression, may be of the same type as described above.

Alternatively, the animal is deficient for a gene or a plurality of genes so that said animal cannot produce or recruit Treg cells. For example, said animal may be deficient in a gene selected from the group consisting of CD28, CCR7, Foxp3, CD25, B7, CCR4, CCR8, ICOS and CCL1. Said animals may be produced according to the methods as above described.

The animal of step a) according to the methods of the invention may be selected from the group consisting of rat, mouse, cow, pig, horse, chicken, cat, and dog. More preferably, the animal is a mouse. Said mouse may be selected from the groups consisting of C57BL/6, BALB/c, DBA/2, CBA/ and SV129 strains.

In the step b) according to the methods of the invention, the arterial blood pressure of the animal may be increased by administering continuously said animal with a compound that may increase the blood volume, arterial resistance (e.g. vasoconstrictors), heart frequency, or blood viscosity. Examples of such compound include but are not limited to angiotensin II, catecholamins (adrenalin or noradrenalin), endothelin 1, aldosterone, and desoxycorticosterone acetate.

The blood pressure of the animal may be superior to 110 mmHg, preferably, superior to 115 mmHg, most preferably superior to 120 mmHg, but may reach values superior to 180 mmHg.

Continuous administering may be performed by any well known method of the art, such as pumps with needle. For example, mini-osmotic pumps (ALZET1002, DURECT CORPORATION) may be used in mice.

Another object of the invention is to provide a non human animal model for aneurysm obtainable according to the methods of the invention.

Such animal model may be useful for screening drugs for treating aneurysm, studying the physiopathology of aneurysm, for testing surgical methods for treating aneurysm, for endeavouring diagnostic or prognostic markers of aneurysm.

Methods of Treatment

In another aspect of the invention, methods and compositions are provided for the prevention or treatment of aneurysm.

The compositions may comprise polypeptides having substantially the same amino acid sequence as TGF-beta.

TGF-beta and variants thereof may be obtained in a variety of ways. They are available from naturally occurring sources, such as bovine bone and human platelets. Methods for their preparation include the following: The peptides may be synthesized on a solid support using various automated synthesizers which are commercially available. Additionally, they may be prepared using recombinant DNA techniques. Thus they may be obtained from growth medium conditioned by Chinese hamster ovary cells (CHO) containing the Simian gene for TGF-beta expressed at high levels by dihydrofolate reductase (dhfr) gene amplification. Methods for obtaining TGF-beta precursor polypeptides and homodimers from transformed CHO cells are described in Gentry et. al. Molecular and Cellular Biology (1987) 7:3417-3427 and U.S. patent application Ser. No. 147,842 filed Jan. 25, 1988, which disclosures are incorporated herein by reference. The TGF-beta or variants thereof also can be prepared by employing recombinant techniques as described in copending U.S. application Ser. No. 148,267 filed Jan. 25, 1988 which disclosure is incorporated herein by reference.

TGF-beta and variants thereof can be purified so as to be substantially free of cellular components employing various purification techniques. These techniques can include solvent extraction, gel permeation chromatography, reversed-phase HPLC, electrophoresis, ion or exchange, affinity chromatography or the like.

Therefore a further object of the invention relates to the use of TGF-beta or a variant thereof for the treatment or the prevention of aneurysm in a subject.

Another object of the invention relates to the use of a nucleic acid encoding for TGF-beta or a variant thereof for the treatment or the prevention of aneurysm in a subject.

Typically, said nucleic acid is a DNA or RNA molecule, which may be included in any suitable vector, such as a plasmid, cosmid, episome, artificial chromosome, phage or a viral vector.

So, a further object of the invention relates to a vector comprising a nucleic acid as above described for the treatment or the prevention of aneurysm in a subject.

Such vectors may comprise regulatory elements, such as a promoter, enhancer, terminator and the like, to cause or direct expression of said polypeptide upon administration to a subject. The vectors may further comprise one or several origins of replication and/or selectable markers. The promoter region may be homologous or heterologous with respect to the coding sequence, and provide for ubiquitous, constitutive, regulated and/or tissue specific expression, in any appropriate host cell, including for in vivo use. Examples of promoters include bacterial promoters (T7, pTAC, Trp promoter, etc.), viral promoters (LTR, TK, CMV-IE, etc.), mammalian gene promoters (albumin, PGK, etc), and the like.

Preferred viruses for certain applications are the adenoviruses and adeno-associated (AAV) viruses, which are double-stranded DNA viruses that have already been approved for human use in gene therapy. Actually 12 different AAV serotypes (AAV1 to 12) are known, each with different tissue tropisms (Wu, Z Mol Ther 2006; 14:316-27). Recombinant AAV are derived from the dependent parvovirus AAV2 (Choi, V W J Virol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Examples of plasmids include replicating plasmids comprising an origin of replication, or integrative plasmids, such as for instance pUC, pcDNA, pBR, and the like. Examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the present invention relates to the use of a cell which has been transfected, infected or transformed by a nucleic acid and/or a vector according to the invention for the treatment or the prevention of aneurysm in a subject. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed". Common expression systems all types of mammalian host cells. Examples of mammalian cells include mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). More particularly, the invention contemplates vascular or endothelial cells thereof or derived thereof, such as human umbilical vein endothelial (HUVEC), progenitor endothelial or smooth muscle cells, or bone marrow-derived (mononuclear or mesenchymal) cells.

A further object of the invention relates to the use of an agonist of TGF-beta-receptor for the treatment or the prevention of aneurysm in a subject.

In a particular embodiment, the TGF-beta-receptor agonist may be a low molecular weight compound, e.g. a small organic molecule.

Alternatively, the TGF-beta agonist may be anti-TGF-beta-receptor antibody. In some embodiments, the TGF-beta-receptor agonist is an antibody that binds to the extracellular domain of at least one TGF-beta receptor and activates said receptor in the same way as for TGF-beta. Such antibodies may be raised according to the same methods as above described.

A further object of the invention relates to the use of an activator of TGF-beta gene expression for the treatment or the prevention of aneurysm in a subject.

A further object of the invention relates to a cellular composition comprising Treg cells for the treatment or the prevention of aneurysm.

Methods for producing Treg cell population are well known in the art (e.g WO2007110785). In particular embodiment, the invention relates to a method for the treatment or the prevention of aneurysm in a subject thereof comprising the steps consisting of:

a) providing a blood sample from said subject
b) isolating the Treg cell population in said sample
c) expanding the Treg cell population of step b)
d) administering the Treg cell population of step c).

A further object of the invention relates to an activator of Treg cells for the treatment or the prevention of aneurysm in a subject in need thereof.

In a particular embodiment, the said activator of Treg cells may be a low molecular weight compound, e.g. a small organic molecule such as an inhibitor of histone deacetylases (HDAC) as described in Tao R et al Nat Med 2007). Histone deacetylases inhibitors are well known in the art and are described in Johnstone R W (2002), and in international patent application no WO2004113366 and WO2007074176. Examples of histone deacetylase inhibitors include but are not limited to trichostatin A (TSA), Apicidin, Sodium Butyrate, (−)-Depudecin, Scriptaid, and Sirtinol. Those compounds may be commercially available from Sigma.

Alternatively, said activator of Treg cells may be an antibody directed against a receptor selected from the group consisting of CD28, CD3 or CTLA-4. Examples of CD28-specific antibodies that can trigger the proliferation of Treg cells are well known in the art and are described in Tacke et al., Eur. J. Immunol., 1997, 27:239-247 and in US2007134240.

Alternatively, said activator of Treg cells may be a cytokine or a growth factor, such as IL-10, or TGF-beta.

The invention will further be illustrated in view of the following figures and example.

EXAMPLE 1

In this example, mouse models for aortic aneurysm according to the invention (obtained either by increasing the arterial blood pressure with angiotensin II and inhibiting the activity of TGFbeta with anti-TGFbeta antibodies; or by increasing the arterial blood pressure with angiotensin II and reducing the number or the activity of Treg cells by knocking-out the CD28 or B7 genes) were tested.

Methods:

Animal Model:

Baseline blood pressure measurements were determined on 5 consecutive days. After these baseline recordings, an osmotic minipump (Alzet Model 2004; DURECT) infusing Angiotensin II (Ang II) (Sigma, St. Louis, Mo.) at a rate of 1,000 ng/kg/min was implanted s.c. and blood pressure measurements continued for 28 days to verify continuous hypertension. The animals ingested either a normal diet containing 0.4% sodium chloride or a high salt diet with 5% sodium chloride (SDS) to accentuate hypertension and kidney injury. All animals studied were between 8 and 14 wk old. The protocol followed the French Department of Agriculture and the National Institute of Health guidelines for animal care and protection. For both strains, all experiments used age- and sex-matched wild-type and genetically altered animals with similar genetic background (C57Bl/6J background). Normal C57Bl/6J and CD28 deficient animals were obtained from Charles River Laboratories. B7.1/B7.2 (CD80/CD86) deficient animals were obtained from Dr. Benoit Salomon (Université Pierre et Marie Curie-CNRS U7087 laboratory, Paris). Anti-pan-TGF-beta antibody (clone 2G7) was administrated thrice a week i.p. at the dose of 500 µg/mouse for two weeks, then at the dose of 150 µg/mouse for the following two weeks. In a subset of experiment, C57Bl6/J mice were treated with a lower dose of anti-TGFBeta Ab (150 µg/mouse three times a week for four weeks). After euthanasia, surgical dissection of the thoraco-abdominal aorta was performed on day 28 or earlier in deceased mice or in mice diagnosed with a complicated AAA by ultrasound examination on day 14 (thrombosis, rupture with parietal hemorrhage and/or dissection).

Figure 5:
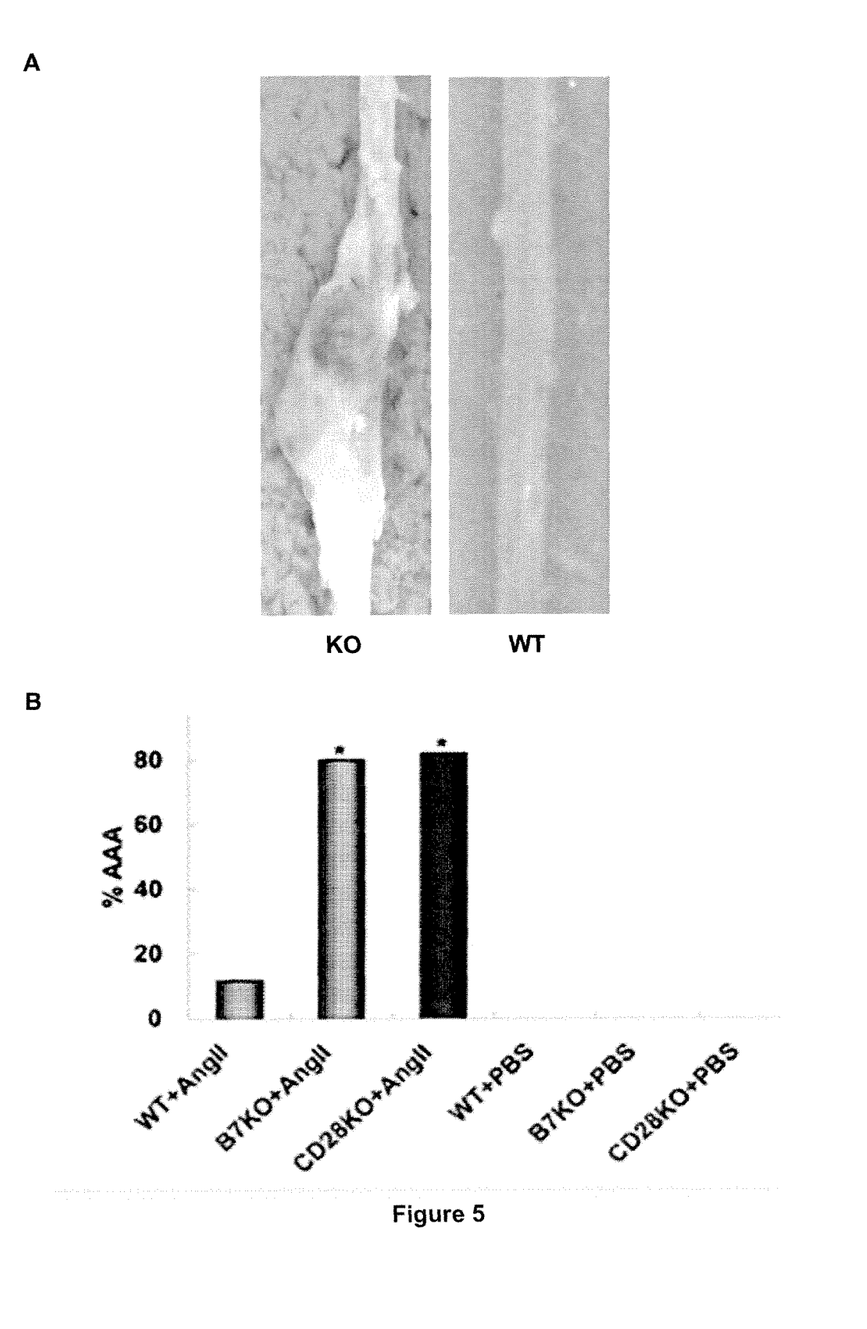
FIG. 5: A. Photography of representative aortas from CD28 KO and WT mice after AngII perfusion. B. Increased proportion of abdominal aortic aneurysm in T regs-deficient CD28−/− and B7−/− hypertensive animals. Both CD28 KO and B7KO (CD80/CD86 deficient) mice displayed increased incidence of AAA upon AngII infusion by comparison with congenic C57Bl6/J controls ($p<0.01$). These two strains are deficient for Tregs, suggesting a critical role for Tregs in preventing the development of AAA. n=5 for each PBS group. n=10 to 17 for AngII groups. *: $p=0.0004$ compared to WT+AngII treated mice.
Figure 6A:
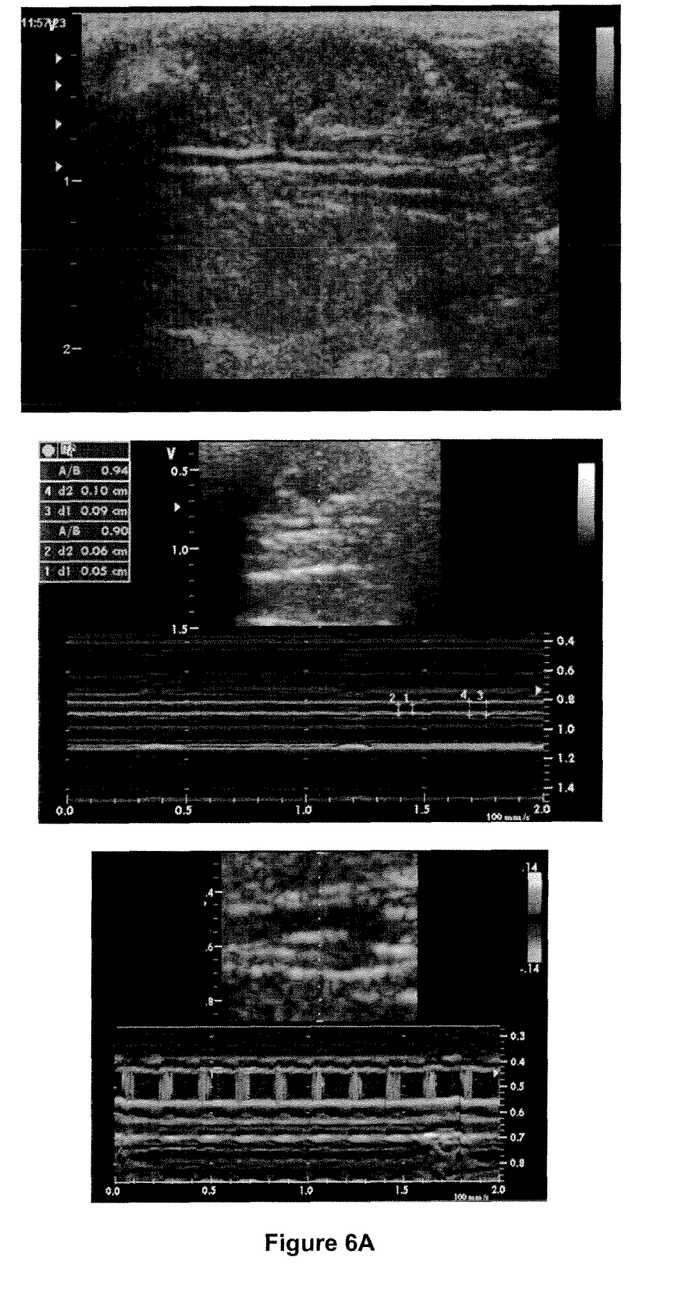
FIG. 6: Representative screen captures after ultrasound evaluation on day 14 of aortic abdominal maximal diameter in a normal hypertensive C57Bl6/J (a: examples of a normal aorta form a WT mouse treated with AngII) and a CD28−/− hypertensive mouse (b: examples of an enlarged aorta from a CD28−/− mouse treated with AngII). Note the larger internal and external aortic diameters in the latter animal. (c) Image of complicated AAA with ruptured arterial wall in hypertensive C57Bl6/J treated with the anti-TGF-beta antibody (examples of ruptured aortas from mice treated with AngII and anti-TGFbeta).
Figure 6B:
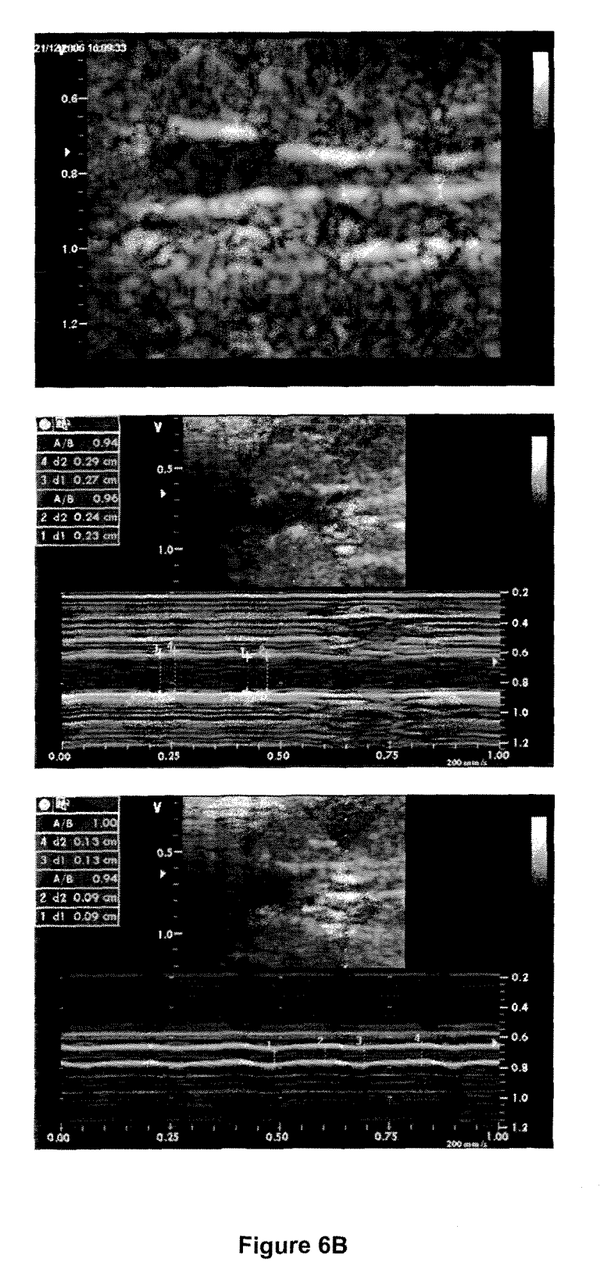
Figure 6C:
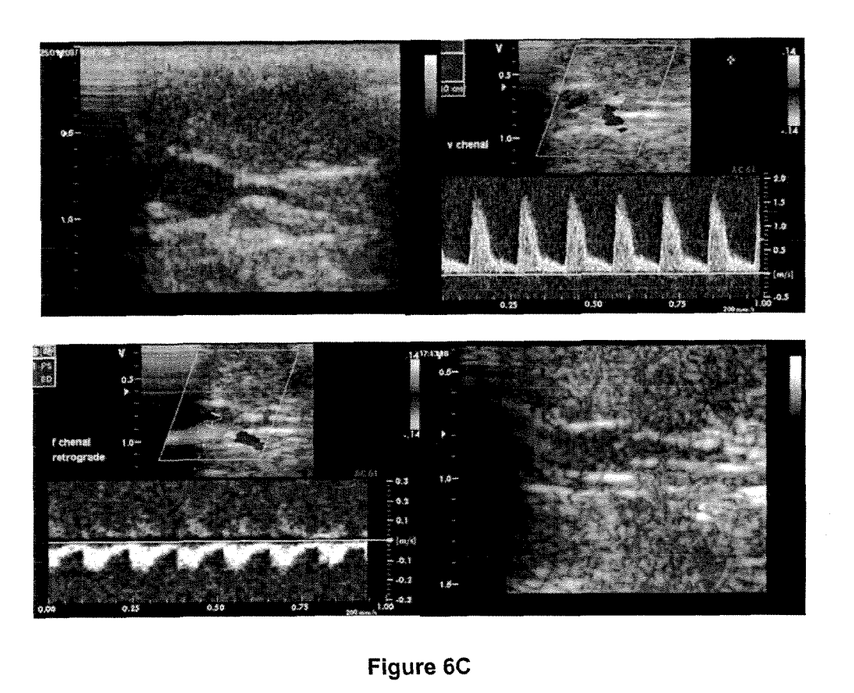

Diagnosis of AAA was performed in vivo on the basis of increased diastolic external diameter of the abdominal aorta assed by ultrasound and color Doppler imaging (see example FIG. 5). Ex vivo, AAA was confirmed by macroscopic segmental weakening and dilatation of the vascular wall. In several instances, retroperitoneal hemorrhage was observed in deceased animals. Final confirmation of AAA was obtained from histopathological evidence of elastin fragmentation, disappearance of vascular smooth muscle cells. Occasionally; luminal or mural thrombus were observed.

Figure 1:
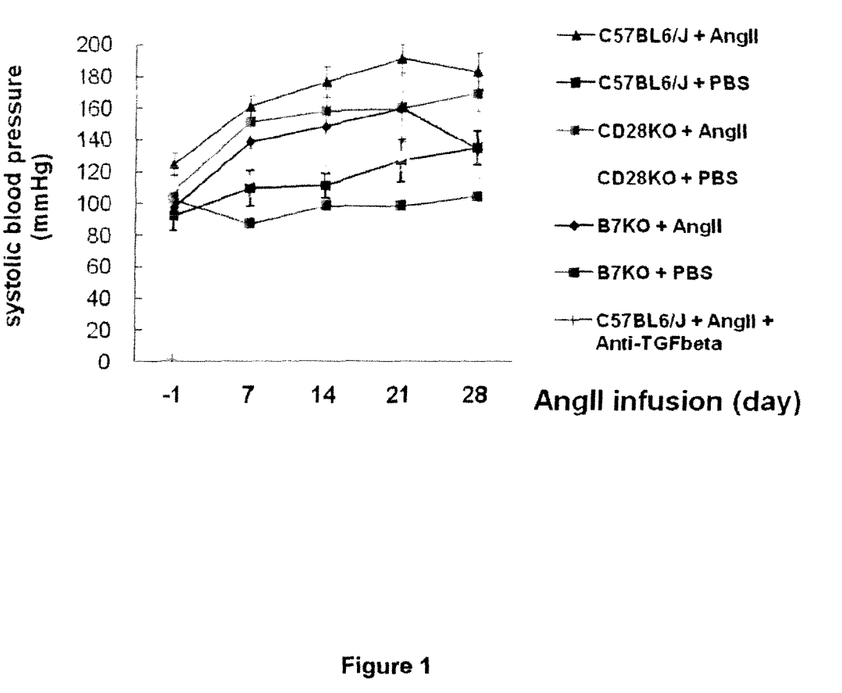
FIG. 1: Evolution of systolic blood pressure in Angiotensin II-chronically infused mice.

Results:

The data of FIG. 1 suggest that neutralization of TGF-beta activity did not influence the pressive action of AngII. Treg deficiency in CD28 KO and B7 KO mice did not significantly altered the AngII-induced high systolic blood pressure. The trend toward lower values at day 28 in these groups was likely related to the severe alteration of perfusion downstream the abdominal aorta in animals with AAA.

Figure 2:
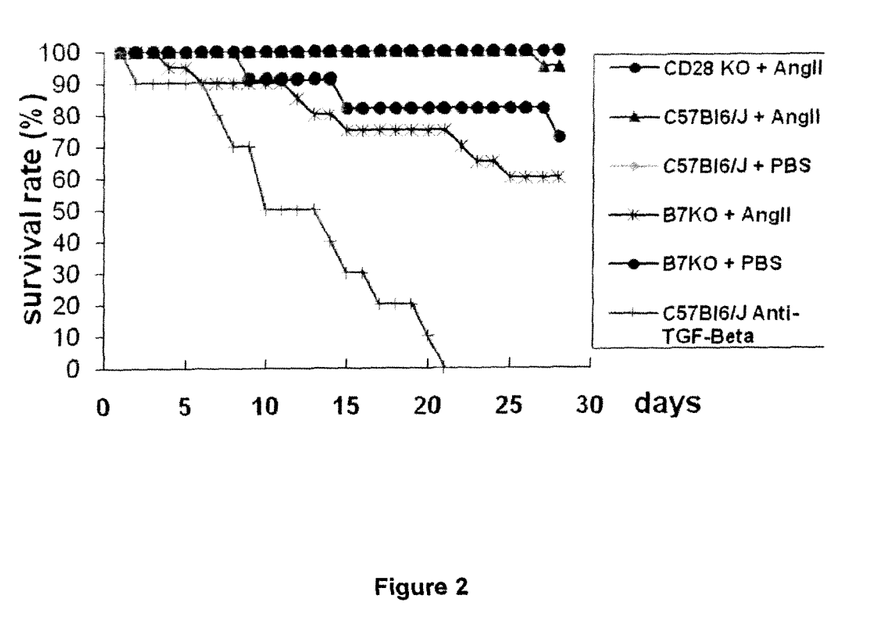
FIG. 2: Survival rate: note the significant higher lower survival rate in normal mice treated with an anti-TGF-Beta antibody or in mice deficient for CD28 or B7 versus hypertensive normal C57Bl6/J mice ($p<0.01$).
Figure 3:
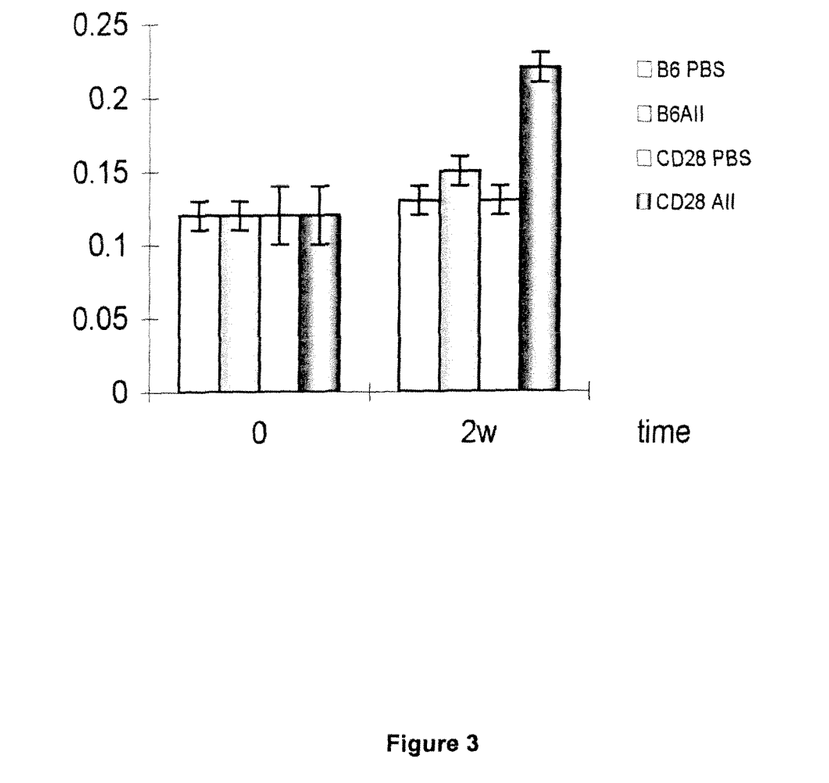
FIG. 3: Ultrasound measurements of the abdominal aorta performed 14 days after angiotensin II infusion revealed increased maximal diastolic aortic diameter (in mm) in Angiotensin II-infused CD28−/− mice by comparison with CD 28+/+ mice. Aortic diameter did not differ between CD28+/+ and CD 28−/− normotensive mice infused with vehicle only.
Figure 4:
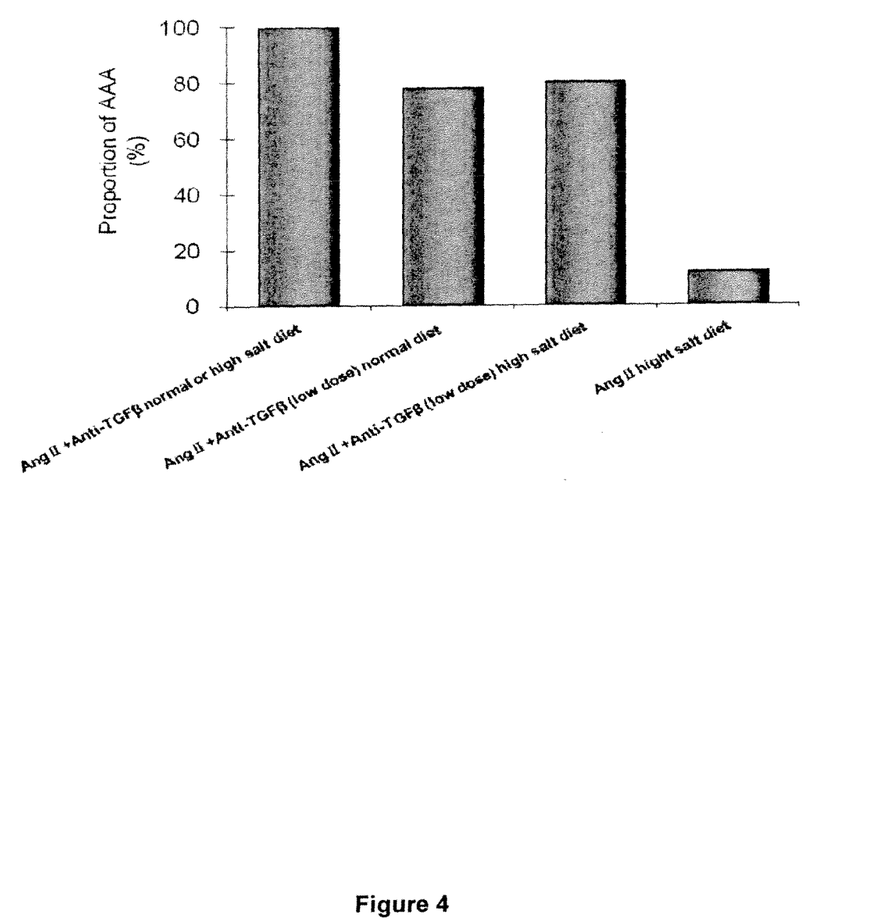
FIG. 4: Proportion of abdominal aortic aneurysms in hypertensive C57Bl6/J mice. Note the significant higher incidence of abdominal aneurysm of the aorta in anti-TGF beta-treated animals at all doses and whatever the sodium chloride content in diet ($P<0.01$ vs. Ang II alone-infused group).

Despite similar levels of systolic blood pressure, hypertensive animals either with impaired TGF-beta activity (C57Bl6/J treated with 2G7 Ab) or with a lack of CD28 or B7 co-stimulatory molecules, exhibited significant higher mortality within 28 days (P<0.01 for each comparison versus C57Bl6/J with AngII alone) (FIG. 2).

In all cases, histopathological analysis of the AAA revealed marked infiltration with T cells (CD3+) indicating unrestrained T cell infiltration. Neutralization of TGF-beta activity in normal mice is expected to block Tregs actions and more specifically, CD28- and B7-deficient animals lack T regulatory cells. Altogether, the similar phenotype (death and AAA with all deaths related to AAA) observed in these three conditions support a critical role of TGF-beta pathway and of Tregs in preventing the development of hypertensive AAA. In the time course of the experiments, hypertension was required to induce AAA in these conditions.

Comparison with Other Models of AAA:

In the first description of the model of angiotensin II/ApoE-model (Daugherty et al.; 2000), the incidence of AAA was reported to be around 33%. Subsequently using the same model, the same authors found that incidence of AAA can vary between 14% (see Babamusta et al, 2006) and 90% (see Thomas et al., 2006). In addition, the severity of aneurysm (extent of dilatation, thrombosis or presence of rupture) in these studies is extremely variable.

In contrast, in our model obtained by increasing the arterial blood pressure with angiotensin II and inhibiting the activity of TGFbeta with anti-TGFbeta antibodies, the incidence of AAA is consistently between 90% and 100%, with consistently more than 70% mortality from aneurysm rupture.

EXAMPLE 2

6 CD28– mice were treated with angiotensin II (as described above) and with 1 mg/kg/day of trichostatin for 14 days. Trichostatin is an inhibitor of Histone Deactylase, known to increase the number of Tregs (Nat Med. 2007 November; 13(11):1299-307).

As shown in Example 1, CD28-mice treated with angiotensin II alone, were highly susceptible to aneurysm and displayed a higher mortality rate than wild-type mice. In contrast, treatment with trichostatin prevented aneurysm in those animals, demonstrating that susceptibility to aneurysm is reduced when Treg function is re-established.

REFERENCES

Babamusta F, Rateri D L, Moorleghen J J, Howatt D A, Li X A, Daugherty A. Angiotensin II infusion induces site-specific intra-laminar hemorrhage in macrophage colony-stimulating factor-deficient mice. Atherosclerosis. 2006 June; 186(2):282-90.

Brummelkamp T R, Bernards R, Agami R. A system for stable expression of short interfering RNAs in mammalian cells. Science. 2002 Apr. 19; 296(5567):550-3.

Chen W., Jin, W., Hardegen, N., Lei, K., Marinos, N., McGrady, G., Wahl, S. Conversion of peripheral CD4+ CD25– naïve T cells to CD4+CD25+ regulatory T cells by TGBbeta induction of transcription factor Foxp3. J Exper Med. 2003 December; 198(12): 1875-86.

Choi V W, Samulski R J, McCarty D M. Effects of adeno-associated virus DNA hairpin structure on recombination. J Virol. 2005 June; 79(11):6801-7.

Colas P, Cohen B, Jessen T, Grishina I, McCoy J, Brent R. (1996) Genetic selection of peptide aptamers that recognize and inhibit cyclin-dependent kinase 2. Nature, 380, 548-50.

Cote R J, Morrissey D M, Houghton A N, Beattie E J Jr, Oettgen H F, Old L J. Generation of human monoclonal antibodies reactive with cellular antigens. Proc Natl Acad Sci USA. 1983 April; 80(7):2026-30.

Daugherty A, Cassis L A. Mouse models of abdominal aortic aneurysms. Arterioscler Thromb Vasc Biol. 2004 March; 24(3):429-34.

Daugherty A, Manning M W, Cassis L A. Angiotensin II promotes atherosclerotic lesions and aneurysms in apolipoprotein E-deficient mice. J Clin Invest. 2000 June; 105 (11):1605-12.

Elbashir S M, Harborth J, Lendeckel W, Yalcin A, Weber K, Tuschl T. Duplexes of 21-nucleotide RNAs mediate RNA interference in cultured mammalian cells. Nature. 2001 May 24; 411(6836):494-8.

Fantini, M., Becker, C., Monteleone, G., Pallone, F., Galle, P., Neurath, M. Cutting edge: TGF-beta induces a regulatory phenotype in CD4+CD25– cells through Fox3p induction and down-regulation of Smad7. J Immunol. 20045149-53.

Faxon D P, Fuster V, Libby P, Beckman J A, Hiatt W R, Thompson R W, Topper J N, Annex B H, Rundback J H, Fabunmi R P, Robertson R M, Loscalzo J; American Heart Association. Atherosclerotic Vascular Disease Conference: Writing Group III: pathophysiology. Circulation. 2004 Jun. 1; 109(21):2617-25.

Gentry L E, Webb N R, Lim G J, Brunner A M, Ranchalis J E, Twardzik D R, Lioubin M N, Marquardt H, Purchio A F. Type 1 transforming growth factor beta: amplified expression and secretion of mature and precursor polypeptides in Chinese hamster ovary cells. Mol Cell Biol. 1987 October; 7(10):3418-27.

Gorelik L, Flavell R A. Transforming growth factor-beta in T-cell biology. Nat Rev Immunol. 2002 January; 2(1):46-53.

Hannon G J. RNA interference. Nature. 2002 Jul. 11; 418 (6894):244-51.

Hogan, B., et al. (Manipulating the mouse embryo. 1994, Second Edition, Cold Spring Harbor Press, Cold Spring Harbor.)

Horwitz, D. Transforming Growth Factor-beta: taking control of T cells' life and death. Immunity. 2006, 25:399-401.

Isselbacher E M. Thoracic and abdominal aortic aneurysms. Circulation. 2005 Feb. 15; 111(6):816-28.

Jayasena S. D. (1999) Aptamers: an emerging class of molecules that rival antibodies in diagnostics. Clin Chem. 45(9):1628-50.

Johnstone R W. Histone-deacetylase inhibitors: novel drugs for the treatment of cancer. Nat Rev Drug Discov. 2002 April; 1(4):287-99.

Joyner, A. L. Gene Targeting. 1999, Second Edition, The Practical Approach Series, Oxford University Press, New York Kohler G, Milstein C. Continuous cultures of fused cells secreting antibody of predefined specificity. Nature. 1975 Aug. 7; 256(5517):495-7.

Kriegler, A Laboratory Manual," W.H. Freeman C.O., New York, 1990.

Lucas C, Bald L N, Fendly B M, Mora-Worms M, Figari I S, Patzer E J, Palladino M A. The autocrine production of transforming growth factor-beta 1 during lymphocyte activation. A study with a monoclonal antibody-based ELISA. J Immunol. 1990 Sep. 1; 145(5):1415-22.

McManus M T, Sharp P A. Gene silencing in mammals by small interfering RNAs. Nat Rev Genet. 2002 October; 3(10):737-47.

Murry, "Methods in Molecular Biology," vol. 7, Humana Press, Inc., Cliffton, N.J., 1991.

Peng Y., Laouar, Y., Li, M., Green, E., Flavell, R. TGF-beta regulates in vivo expansion of Foxp3-expressing CD4+ CD25+ regulatory T cells responsible for protection against diabetes. PNAS, 2004, 101(13): 4572-77/

Seong E, Saunders T L, Stewart C L, Burmeister M. To knockout in 129 or in C57BL/6: that is the question. Trends Genet. 2004 February; 20(2):59-62.

Stroschein S L, Wang W, Zhou S, Zhou Q, Luo K. Negative feedback regulation of TGF-beta signaling by the SnoN oncoprotein. Science. 1999 Oct. 22; 286(5440):771-4.

Tao R, de Zoeten E F, Ozkaynak E, Chen C, Wang L, Porrett P M, Li B, Turka L A, Olson E N, Greene M I, Wells A D, Hancock W W. Deacetylase inhibition promotes the generation and function of regulatory T cells. Nat Med. 2007 Oct. 7.

Thomas M, Gavrila D, McCormick M L, Miller F J Jr, Daugherty A, Cassis L A, Dellsperger K C, Weintraub N L. Deletion of p47phox attenuates angiotensin II-induced abdominal aortic aneurysm formation in apolipoprotein E-deficient mice. Circulation. 2006 Aug. 1; 114(5): 404-13.

Thompson R W, Geraghty P J, Lee J K. Abdominal aortic aneurysms: basic mechanisms and clinical implications. Curr Probl Surg. 2002 February; 39(2):110-230.

Tuerk C., Using the SELEX combinatorial chemistry process to find high affinity nucleic acid ligands to target molecules. Methods Mol Biol. 1997; 67: 219-30.

Tuschl T, Zamore P D, Lehmann R, Bartel D P, Sharp P A. Targeted mRNA degradation by double-stranded RNA in vitro. Genes Dev. 1999 Dec. 15; 13(24):3191-7.

Wolfer D P, Crusio W E, Lipp H P. Knockout mice: simple solutions to the problems of genetic background and flanking genes. Trends Neurosci. 2002 July; 25(7):336-40.

Wu Z, Asokan A, Samulski R J. Adeno-associated virus serotypes: vector toolkit for human gene therapy. Mol Ther. 2006 September; 14(3):316-27. Epub 2006 Jul. 7.

Yamagiwa, S., Gray, J., Hashimoto, S., Horwitz, D. A role for TGF-beta in the generation and expansion of CD4+CD25+ regulatory T cells from human peripheral blood. J Immunol., 2001, 7282-89.

The invention claimed is:

1. A method for producing a non human animal model for aortic aneurysm comprising the steps consisting of:
   a) providing a non human animal;
   b) increasing the arterial blood pressure of said animal;
   c) inhibiting the activity of Transforming Growth Factor Beta (TGF-beta) in said animal to provide a treated animal,
   wherein the treated animal displays a greater incidence of aortic aneurysm when compared to a non human animal not having the activity of TGF-beta inhibited.

2. The method according to claim 1 wherein at step c) an antagonist of TGF-beta is used.

3. The method according to claim 2 wherein said antagonist is a neutralizing anti-TGF-beta antibody.

4. The method according to claim 1 wherein at step c) the activation of the TGF-beta gene expression is inhibited.

5. A method for producing a non human animal model for aortic aneurysm comprising the steps consisting of:
   a) providing a non human animal;
   b) increasing the arterial blood pressure of said animal;
   c) reducing the number or the activity of Treg cells in said animal to provide a treated animal,
   wherein the treated animal displays a greater incidence of aortic aneurysm when compared to a non human animal not having the number or the activity of Treg cells reduced.

6. The method according to claim 5 wherein said animal is deficient in a gene selected from the group consisting of CD28, CCR7, Foxp3, CD25, B7, CCR4, CCR8, ICOS and CCL1.

7. The method according to claim 5 wherein at step c) the Treg cells are depleted.

8. The method according to claim 1 wherein said non human animal is a mouse.

9. The method according to claim 1 wherein the animal is administered a continuous amount of a compound selected in the group consisting of Angiotensin II, catecholamins, endothelin 1, aldosterone, and desoxycorticosterone acetate.

10. A non human animal model obtainable by a method according to claim 1.

* * * * *